United States Patent
Aoyagi et al.

(10) Patent No.: US 8,024,021 B2
(45) Date of Patent: Sep. 20, 2011

(54) TIME-SEGMENTED PULSE OXIMETRY AND PULSE OXIMETER PERFORMING THE SAME

(75) Inventors: Takuo Aoyagi, Tokyo (JP); Masayoshi Fuse, Tokyo (JP); Naoki Kobayashi, Tokyo (JP)

(73) Assignee: Nihon Kohden Corporation, Tokyo (JP)

(*) Notice: Subject to any disclaimer, the term of this patent is extended or adjusted under 35 U.S.C. 154(b) by 1422 days.

(21) Appl. No.: 11/511,476

(22) Filed: Aug. 29, 2006

(65) Prior Publication Data

US 2007/0049812 A1 Mar. 1, 2007

(30) Foreign Application Priority Data

Aug. 30, 2005 (JP) ................ P2005-248922

(51) Int. Cl.
*A61B 5/1455* (2006.01)
(52) U.S. Cl. .................. 600/336; 600/323
(58) Field of Classification Search ........... 600/309–344
See application file for complete search history.

(56) References Cited

U.S. PATENT DOCUMENTS

| | | | | |
|---|---|---|---|---|
| 5,503,148 | A | * | 4/1996 | Pologe et al. ............ 600/323 |
| 5,577,500 | A | * | 11/1996 | Potratz ................... 600/330 |
| 5,766,125 | A | | 6/1998 | Aoyagi et al. |
| 6,230,035 | B1 | | 5/2001 | Aoyagi et al. |
| 2005/0049469 | A1 | | 3/2005 | Aoyagi et al. |

FOREIGN PATENT DOCUMENTS

| JP | 5-88609 B2 | 12/1993 |
|---|---|---|
| JP | 11-216133 A | 8/1999 |
| JP | 2005-95606 A | 4/2005 |

* cited by examiner

*Primary Examiner* — Eric F Winakur
*Assistant Examiner* — Chu Chuan Liu
(74) *Attorney, Agent, or Firm* — Sughrue Mion, PLLC

(57) ABSTRACT

To measure oxygen saturation in blood, living tissue is irradiated with a first light beam having a first wavelength and a second light beam having a second wavelength. A first electrical signal is generated from the first light beam reflected from or transmitted through the tissue. A second electrical signal is generated from the second light beam reflected from or transmitted through the tissue. The first electrical signal is divided into a plurality of first segments, each including a part of the first electrical signal for a predetermined time period. The second electrical signal is divided into a plurality of second segments, each including a part of the second electrical signal for the predetermined time period. A gradient of a regression line is calculated between every one of the first segments and an associated one of the second segments, thereby obtaining a plurality of gradients.

6 Claims, 4 Drawing Sheets

TIME-SEGMENTED PULSE OXIMETRY AND PULSE OXIMETER PERFORMING THE SAME

BACKGROUND OF THE INVENTION

The present invention relates to pulse oximetry for continuously measuring arterial oxygen saturation ($SaO_2$) in a non-invasive manner by use of changes in arterial blood volume in tissue caused by pulsation, as well as to a pulse oximeter for performing the same. More specifically, the present invention relates to time-segmented pulse oximetry capable of obtaining arterial oxygen saturation with high accuracy, as well as to a pulse oximeter capable of performing the same.

A so-called "pulse oximetry" method currently adopts the following procedures for obtaining arterial oxygen saturation ($SaO_2$):

(1) light beams having different wavelengths (e.g., denoted as i and j) and transmitted through tissue are continuously measured;

(2) a peak and a bottom in pulsation of the light transmitted through the tissue to be measured are determined, and a transmitted light beam at the peak and that at the bottom are respectively defined as $Li+\Delta Li$ and $Li$, $Lj+\Delta Lj$ and $Lj$;

(3) $\Delta A$ (attenuation change) is calculated from the following expression:

$$\Delta Ai = \log[(Li+\Delta Li)/Li] \approx \Delta Li/Li;$$

$$\Delta Aj = \log[(Lj+\Delta Lj)/Lj] \approx \Delta Lj/Lj;$$

(4) $\Phi ij$ (attenuation change ratio) is calculated from the following expression:

$$\Phi ij = \Delta Ai/\Delta Aj; \text{ and}$$

(5) since $\Phi ij$ corresponds to $SaO_2$ in a proportion of approximately one to one, $\Phi ij$ is converted into $SaO_2$.

A currently available apparatus for measurement of arterial oxygen saturation employs a conversion table for conversion of $\Phi ij$ into $SaO_2$. In a case where such an apparatus is configured to use two wavelengths of light beams, no specific problems is encountered in using the conversion table. However, in a case of an apparatus which uses three or more wavelengths of light beams so as to enhance measurement accuracy, the conversion must be performed on the basis of calculation formulae obtained theoretically and experimentally.

For instance, Japanese Patent Publication No. 2005-95606A discloses an oximeter which irradiates a living tissue with five light beams which differ in wavelength, as apparatus for continuously measuring arterial oxygen saturation in a non-invasive manner by use of blood volume changes of arterial blood due to pulsation.

Disturbance in transmitted light caused by mechanical disturbance, such as a body motion, has long posed a problem for pulse oximetry. More specifically, when transmitted light is disturbed, appropriate detection of peaks and bottoms of measured pulse waveforms encounters difficulty. In addition, correction of the peaks and bottoms of the measured pulse waveforms is required. When the correction is not performed, time series data pertaining to an arterial oxygen saturation ($SaO_2$) to be obtained in a final step include a problem of an increase in error. In addition, utilization of information other than the values of the peaks and bottoms becomes essential for elimination of artifacts by the body motion.

In a case where body motions of a patient are extremely vigorous, the conventional pulse oximetry based on determination of peaks and bottoms of pulse waveforms of measured transmitted light has been found to be unable to obtain satisfactory measurement results. More specifically, when body motions are vigorous, the peaks and bottoms of the measured waveforms cannot be uniquely determined. Therefore, there arises a problem that even a technique making use of, e.g., base line correction of the measured waveforms, cannot be expected to exert sufficient effects.

A method having conventionally been proposed or adopted as a countermeasure to solve such a problem is a statistical method of estimating an accurate $SaO_2$ value on the basis of data at time points before and after the target point. However, employment of this method includes the following problems:

(1) since a long time delay is developed, detection of, e.g., a start of decrease in $SaO_2$ is delayed; and (2) since changes in $SaO_2$ are smoothed, even when, e.g., $SaO_2$ falls steeply, the degree of the decrease involves uncertainty.

SUMMARY OF THE INVENTION

It is therefore an object of the invention to provide time-segmented pulse oximetry and a pulse oximeter performing the same, thereby eliminating artifacts exerted by body motions, and contributing to improvement of measurement accuracy of an arterial oxygen saturation ($SaO_2$).

In order to achieve the above object, according to the invention, there is provided a method of measuring an oxygen saturation in blood of a subject, comprising:

irradiating a living tissue of the subject with a first light beam having a first wavelength and a second light beam having a second wavelength different from the first wavelength;

generating a first electrical signal from the first light beam reflected from or transmitted through the living tissue;

generating a second electrical signal from the second light beam reflected from or transmitted through the living tissue;

dividing the first electrical signal into a plurality of first segments each of which includes a part of the first electrical signal for a predetermined time period;

dividing the second electrical signal into a plurality of second segments each of which includes a part of the second electrical signal for the predetermined time period; and calculating a gradient of a regression line between every one of the first segments and an associated one of the second segments, thereby obtaining a plurality of gradients.

The method may further comprise: calculating an arterial oxygen saturation from every one of the gradients, thereby obtaining a plurality of arterial oxygen saturations; smoothing the arterial oxygen saturations to obtain a smoothed arterial oxygen saturation; and calculating an oxygen saturation in blood based on the smoothed arterial oxygen saturation.

Alternatively, the method may further comprise: smoothing the gradients to obtain a smoothed gradient; calculating an arterial oxygen saturation from the smoothed gradient; and calculating an oxygen saturation in blood based on the arterial oxygen saturation.

According to the invention, there is also provided a pulse oximeter operable to measure an oxygen saturation in blood of a subject, comprising:

a light emitter, adapted to irradiate a living tissue of the subject with a first light beam having a first wavelength and a second light beam having a second wavelength different from the first wavelength;

a signal generator, operable to generate a first electrical signal from the first light beam reflected from or transmitted through the living tissue, and operable to generate a second electrical signal from the second light beam reflected from or transmitted through the living tissue; and a processor, operable to:
divide the first electrical signal into a plurality of first segments each of which includes a part of the first electrical signal for a predetermined time period;
divide the second electrical signal into a plurality of second segments each of which includes a part of the second electrical signal for the predetermined time period; and
calculate a gradient of a regression line between every one of the first segments and an associated one of the second segments, thereby obtaining a plurality of gradients.

The processor may be operable to: calculate an arterial oxygen saturation from every one of the gradients, thereby obtaining a plurality of arterial oxygen saturations; smooth the arterial oxygen saturations to obtain a smoothed arterial oxygen saturation; and calculate an oxygen saturation in blood based on the smoothed arterial oxygen saturation.

Alternatively, the processor may be operable to: smooth the gradients to obtain a smoothed gradient; calculate an arterial oxygen saturation from the smoothed gradient; and calculate an oxygen saturation in blood based on the arterial oxygen saturation.

With the above configurations, since not only data pertaining to peaks and bottoms of the signals generated from the detected light beams, but also the entirety of time series data pertaining to the detected light beams is used, determination of the peaks and the bottoms of the signals is not necessary. Therefore, artifacts exerted by body motions are eliminated, and contribution to improvement of measurement accuracy of an arterial oxygen saturation ($SaO_2$) is attained, thereby increasing flexibility in relation to the measurement position to which the light emitter is attached.

BRIEF DESCRIPTION OF THE DRAWINGS

The above objects and advantages of the present invention will become more apparent by describing in detail preferred exemplary embodiments thereof with reference to the accompanying drawings, wherein.

DETAILED DESCRIPTION OF THE EMBODIMENTS

Embodiments of the invention will be described below in detail with reference to the accompanying drawings.

Figure 1:
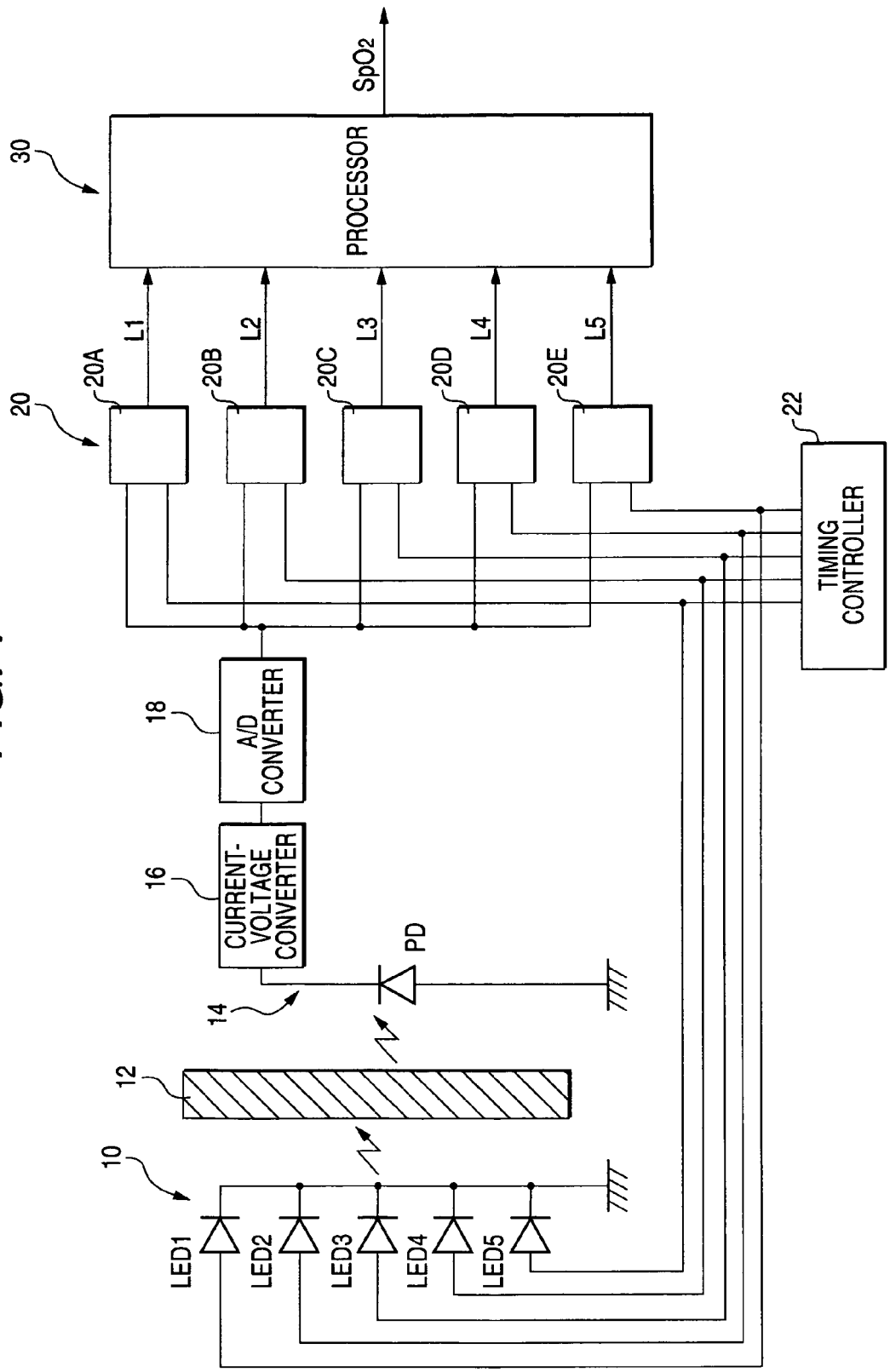
FIG. 1 is a block diagram showing a pulse oximeter according to one embodiment of the invention.

As shown in FIG. 1, a pulse oximeter according to one embodiment of the invention comprises a light emitter 10 which has five light emitting diodes LED 1 to LED 5 for irradiating a living tissue 12 with five light beams which differ in wavelength; a light receiver 14 which comprises a photo diode PD for receiving light transmitted through the living tissue 12; a current-voltage converter 16; and an A/D converter 18.

A storage section 20 comprises temporary storage devices 20A to 20E which store transmitted light signals acquired by the photo diode PD in the light receiver 14 as time series data for the respective wavelengths.

A processor 30 calculates an oxygen saturation in blood ($SpO_2$) on the basis of transmitted light signals L1 to L5, which are temporarily stored in the respective temporary storage devices 20A to 20E. This processing is realized by the following procedures:

(1) dividing each of the respective transmitted light signals L1 to L5 into predetermined time segments;

(2) subsequently calculating gradients of regression lines, each of which pertains to two data sets on different wavelengths among the time series data pertaining to the transmitted light signals L1 to L5 having been divided into predetermined time segments;

(3) converting the thus-calculated gradients into respective values of $SaO_2$ (arterial oxygen saturations); and (4) smoothing the thus-converted time series data pertaining to $SaO_2$, thereby calculating an oxygen saturation in blood ($SpO_2$). In the above, the conversion into $SaO_2$ and smoothing may be performed in the reverse order.

A timing controller 22 is configured so as to control a timing at which each of the light-emitting diodes LED 1 to LED 5 of the light emitter 10 illuminates, and a timing at which each of the temporary storage devices 20A to 20E in the storage section 20 stores the transmitted light signals L1 to L5.

Figure 2:
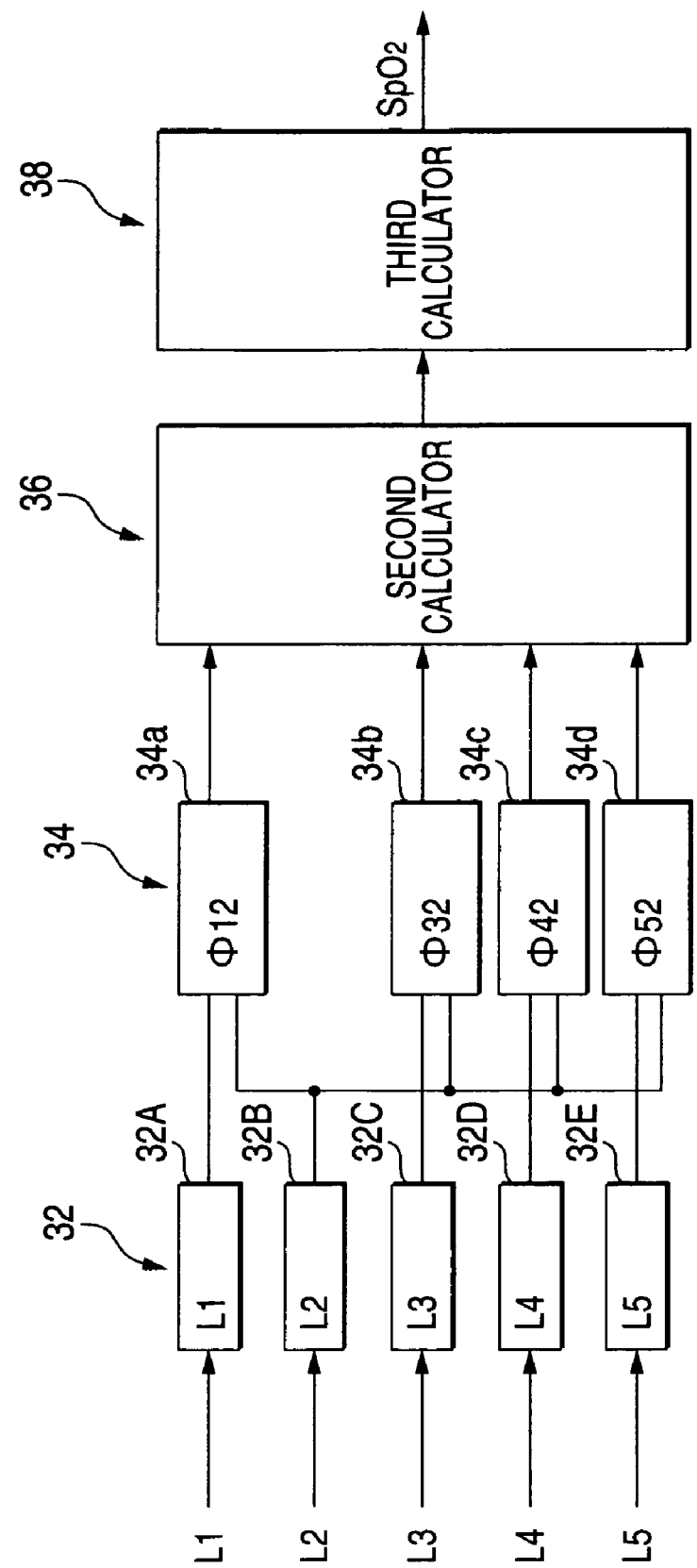
FIG. 2 is a block diagram showing a system configuration of a processor in the pulse oximeter.

As shown in FIG. 2, the processor 30 comprises a segmented data storage element 32 including storage elements 32A to 32E which divide the transmitted light signals L1 to L5, having been input from the temporary storage devices 20A to 20E, into data pieces corresponding to segments of a predetermined time period (e.g., 0.5 second), and sequentially store the segmented data pieces as time series data.

The processor 30 further comprises a first calculator 34 including calculator elements 34a, 34b, 34c and 34d which respectively calculate gradients Φ12, Φ32, Φ42, and Φ52 of regression lines with regard to the transmitted light signals L1 to L5 having been stored in the segmented data storage element 32 as the segmented data pieces.

The processor 30 further comprises: a second calculator 36 which obtains solutions to simultaneous equations with regard to the gradients Φ12, Φ32, Φ42, and Φ52 of the regression lines having been obtained by the first calculator 34; and a third calculator 38 which smoothes the solutions of the simultaneous equations, thereby obtaining an oxygen saturation in blood ($SpO_2$). Meanwhile, the solutions may be determined after the gradients have been smoothed.

Next, processing operations for calculating an arterial oxygen saturation performed by apparatus having the configuration of the above-described pulse oximeter; that is, the time-segmented pulse oximetry according to the present invention, will be described.

First, the light emitting elements LED 1 to LED 5 of the light emitter 10 are caused to illuminate sequentially and alternately with different wavelengths λ1, λ2, λ3, λ4, and λ5 in accordance with signals output from the timing controller 22. When illumination is effected, light transmitted through the living tissue 12 is received by the light receiver 14. The transmitted light signals L1, L2, L3, L4, and L5 are respectively stored, at predetermined timings, in the respective temporary storage devices 20A to 20E of the storage section 20. Meanwhile, the temporary storage devices 20A to 20E store data (digital values) having been output from the A/D converter 18 of the light-receiving device 14, for a predetermined duration.

As described above, the transmitted light signals L1 to L5 respectively stored in the temporary storage devices 20A to 20E are respectively input to the respective segmented data storage elements 32A to 32E of the segmented data storage 32 in the processor 30, and divided into data pieces corresponding to segments of a predetermined time period (e.g., 0.5 second). The segmented data pieces are sequentially stored as time series data.

An oxygen saturation in blood ($SpO_2$) is calculated from the following expressions, as a ratio ($\Phi ij$, where i and j are wavelengths) between attenuation changes, on the basis of attenuation changes ($\Delta Ai$) obtained with regard to transmitted light beams of, e.g., five wavelengths. Meanwhile, constituents of pulsation of transmitted light are arterial blood (a), venous blood (v), and tissue (t) other than blood; that is, pure tissue.

$$\Phi ij \equiv \frac{\Delta Ai}{\Delta Aj} = \frac{\sqrt{Eai(Eai+F)} + \sqrt{(Evi(Evi+F)}\,V + Exi}{\sqrt{Eaj(Eaj+F)} + \sqrt{(Evj(Evj+F)}\,V + Exj}$$

where $\Delta Ai \equiv \log[(Li+\Delta Li)/Li] \approx \Delta Li/Li$, $Eai \equiv Sa \cdot Eoi + (1-Sa)Eri$, $Evi \equiv Sv \cdot Eoi + (1-Sv)Eri$, $V \equiv \Delta Dv/\Delta Da$, and $Exi \equiv Zti \cdot \Delta Dt/(Hb \cdot \Delta Da) \equiv Ai \cdot Ex2 + Bi$.

In the above expressions, Li is light transmitted through tissue; $\Delta Ai$ is an attenuation change; Eoi is a light absorbing coefficient of oxygenated hemoglobin; Eri is a light absorbing coefficient of deoxygenated hemoglobin; Sa is arterial oxygen saturation ($SaO_2$); Sv is peripheral venous oxygen saturation ($SvO_2$); Hb is a hemoglobin concentration; $\Delta Da$ is a change in effective thickness of arterial blood; $\Delta Dv$ is a change in effective thickness of venous blood; $\Delta Dt$ is a change in effective thickness of the pure tissue; Zti is a constant of attenuation by the pure tissue; Ex2 is a value of Exi at a second wavelength; and Ai and Bi are tissue constants (determined by actual measurement). Therefore, the above expressions include four unknowns consisting of Sa, Sv, V, and Ex2.

In this case, Sa can be calculated as a solution to simultaneous equations with four unknowns. The equations are formulated on the basis of measurement of transmitted light beams of five appropriate wavelengths so as to measure $SaO_2$ with high accuracy and eliminate artifacts exerted by body motions, and the like. Examples of the five wavelengths include a set consisting of: $\lambda 1=805$ nm, $\lambda 2=875$ nm, $\lambda 3=660$ nm, $\lambda 4=700$ nm, and $\lambda 5=730$ nm.

In the time-segmented pulse oximetry of the invention, gradients ($\Phi ij$) of the respective regression lines are determined from the following expressions on the basis of the transmitted light signals L1 to L5 of the five wavelengths ($\lambda 1$ to $\lambda 5$) having been divided into time segments and stored in the segmented data storage element 32. Put another way, the gradients ($\Phi ij$) in this case correspond to $\Delta Ai/\Delta Aj$, which are described above. In the following expression, "n" is a count of data sets within a divided time segment, "t" is a period of time (e.g., 0.5 second) of the divided time segment, and $\Sigma$ is a sum of data within a time segment.

$$\Phi ij \equiv \frac{n\sum Li(t)Lj(t) - \sum Li(t)\sum Lj(t)}{[n\sum Lj(t)^2] - [\sum Lj(t)]^2}$$

Simultaneous equations with four unknowns in relation to the gradients ($\Phi 12$, $\Phi 32$, $\Phi 42$, and $\Phi 52$) of the regression lines pertaining to the five wavelength light beams ($\lambda 1$ to $\lambda 5$) transmitted through the tissue are formulated on the basis of the above expressions, and Sa is calculated as a solution to the simultaneous equations.

The value of Sa obtained as the solution to the simultaneous equations with four unknowns is calculated by dividing data, which are continuous in time, into time segments. Therefore, the value of Sa exhibits large variations on a time segment basis. To this end, smoothing of Sa is performed. By virtue of the smoothing, there can be obtained a natural change in $SaO_2$.

An example calculation result of arterial oxygen saturation ($SaO_2$) on a subject in accordance with the time-segmented pulse oximetry according to the present invention will be described on the basis of comparison with that in accordance with a conventional pulse oximetry method by reference to graphs indicating the respective measurement results.

Figure 3:
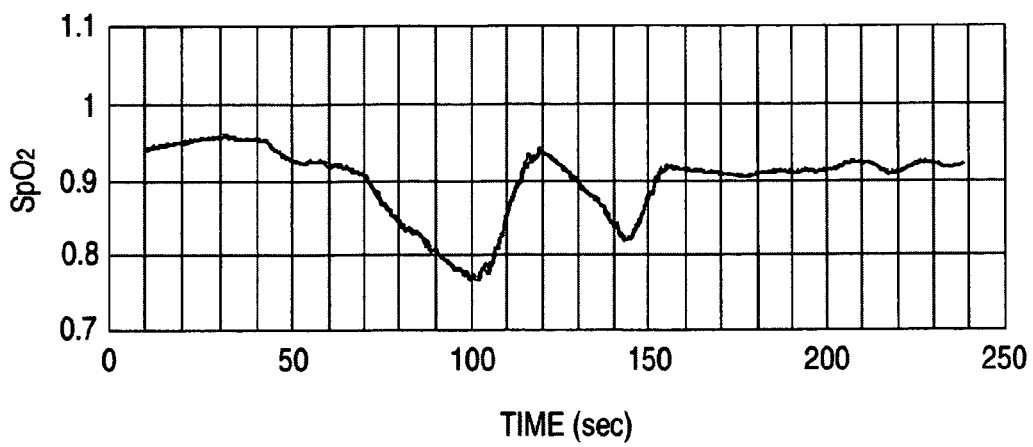
FIG. 3 is a graph showing a waveform of $SpO_2$ measured by the pulse oximeter.
Figure 4:
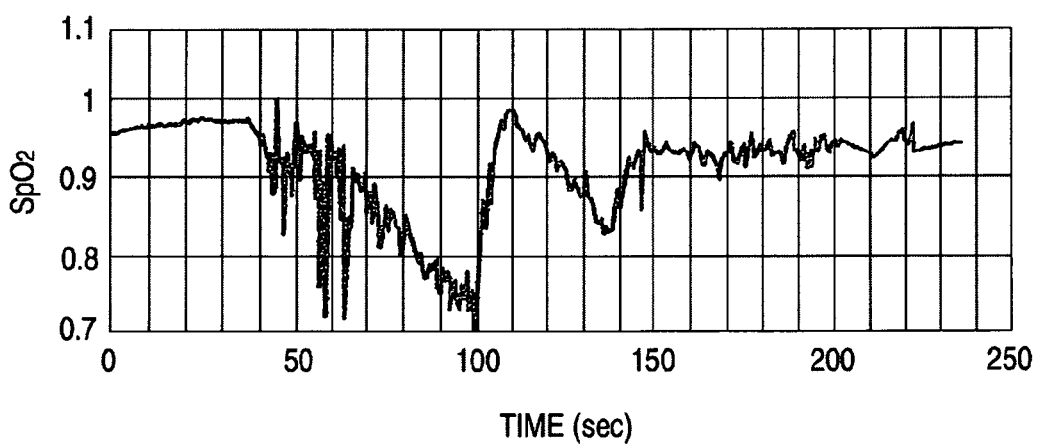
FIG. 4 is a graph showing a waveform of $SpO_2$ measured by a pulse oximeter according to a first comparative example.
Figure 5:
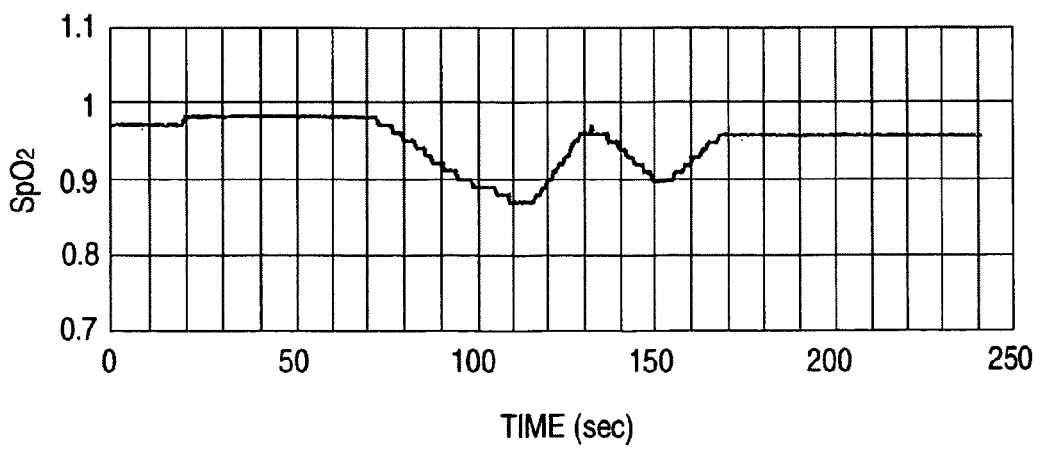
FIG. 5 is a graph showing a waveform of $SpO_2$ measured by a pulse oximeter according to a second comparative example.

The light emitter 10 and the light receiver 14 were attached to a finger tip of the subject. The value of $SpO_2$ was measured in a state where $SaO_2$ was caused to decrease by breath holding, while the patient vigorously shook his/her hand from the wrist in a chopping manner. FIG. 3 shows changes in $SpO_2$ measured in accordance with the time-segmented pulse oximetry of the invention with five wavelengths. FIG. 4 shows changes in $SpO_2$ measured in accordance with the conventional two-wavelength calculation (in this case, operations for eliminating body motions were not performed). FIG. 5 shows changes in $SpO_2$ which were measured with a commercially-available pulse oximeter attached to the other hand.

As shown in the drawings, the time-segmented pulse oximetry of the invention could sufficiently eliminate artifacts exerted by the body motions. In addition, a rapid change in $SaO_2$ was explicitly detected. In particular, the pulse oximetry was confirmed to be capable of detecting, at an early timing, a point in time where a decrease in $SaO_2$ started.

Figure 6A:
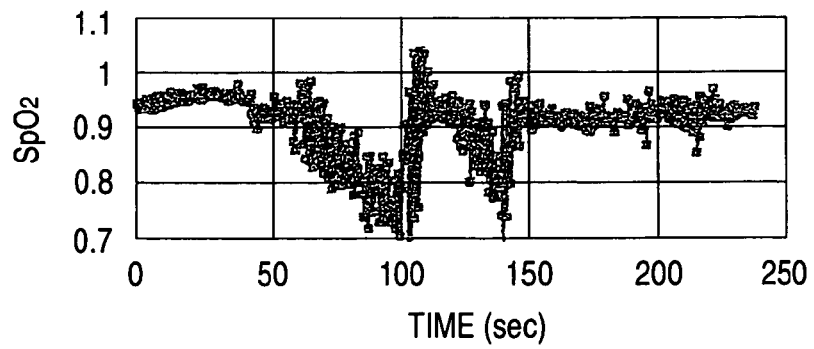
FIGS. 6A to 6C are graphs showing results of smoothing performed with respect to the waveform of $SpO_2$ measured by the pulse oximeter.
Figure 6B:
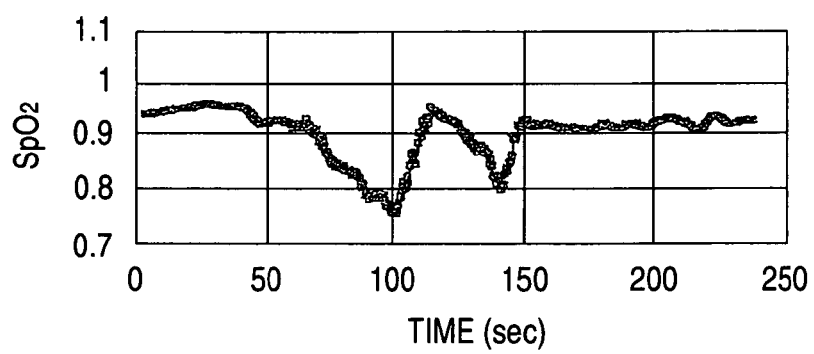
Figure 6C:
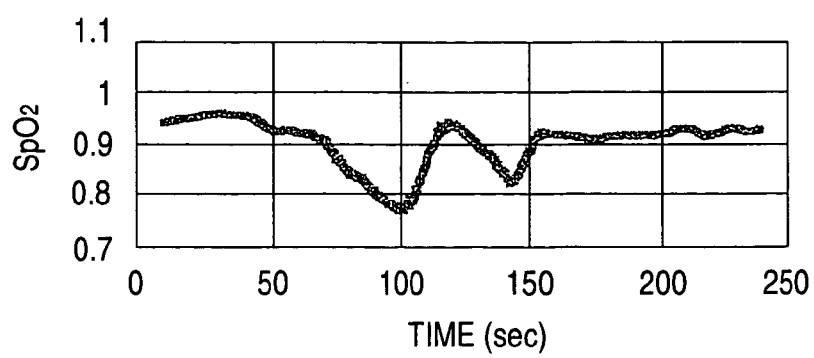

FIG. 6A shows a waveform indicating $SpO_2$ values calculated by the second calculator 36 as solutions to the simultaneous equations with four unknowns related to the gradients $\Phi 12$, $\Phi 32$, $\Phi 42$, and $\Phi 52$ of the regression lines, and shows a state where no smoothing was performed. FIG. 6B shows a state where 10 data sets were averaged and smoothed by the third calculator 38, and FIG. 6C shows a state where 20 data sets were similarly averaged and smoothed.

In the above embodiment, the case where five wavelengths are used. However, the number of the wavelengths may be greater or smaller than five. In addition, the invention can be applied to all objects of measurement which pulsate with pulsation of arterial blood. More specifically, examples of such an object to be measured include CO hemoglobin in blood, and a dilution state of a dye injected from outside of a body. The invention may be modified in various manners without departing from the scope of the invention.

What is claimed is:
1. A method of measuring an oxygen saturation in blood of a subject, comprising:

irradiating a living tissue of the subject with a first light beam having a first wavelength and a second light beam having a second wavelength different from the first wavelength;

generating a first electrical signal from the first light beam reflected from or transmitted through the living tissue;

generating a second electrical signal from the second light beam reflected from or transmitted through the living tissue;

dividing the first electrical signal into a plurality of first segments each of which includes a part of the first electrical signal for a predetermined time period;

dividing the second electrical signal into a plurality of second segments each of which includes a part of the second electrical signal for the predetermined time period; and calculating a gradient of a regression line between every one of the first segments and an associated one of the second segments, thereby obtaining a plurality of gradients.

2. The method as set forth in claim 1, further comprising:

calculating an arterial oxygen saturation from every one of the gradients, thereby obtaining a plurality of arterial oxygen saturations;

smoothing the arterial oxygen saturations to obtain a smoothed arterial oxygen saturation; and calculating an oxygen saturation in blood based on the smoothed arterial oxygen saturation.

3. The method as set forth in claim 1, further comprising:

smoothing the gradients to obtain a smoothed gradient;

calculating an arterial oxygen saturation from the smoothed gradient; and calculating an oxygen saturation in blood based on the arterial oxygen saturation.

4. A pulse oximeter operable to measure an oxygen saturation in blood of a subject, comprising:

a light emitter, adapted to irradiate a living tissue of the subject with a first light beam having a first wavelength and a second light beam having a second wavelength different from the first wavelength;

a signal generator, operable to generate a first electrical signal from the first light beam reflected from or transmitted through the living tissue, and operable to generate a second electrical signal from the second light beam reflected from or transmitted through the living tissue;

a processor, operable to:

divide the first electrical signal into a plurality of first segments each of which includes a part of the first electrical signal for a predetermined time period;

divide the second electrical signal into a plurality of second segments each of which includes a part of the second electrical signal for the predetermined time period; and calculate a gradient of a regression line between every one of the first segments and an associated one of the second segments, thereby obtaining a plurality of gradients.

5. The pulse oximeter as set forth in claim 4, wherein:

the processor is operable to:

calculate an arterial oxygen saturation from every one of the gradients, thereby obtaining a plurality of arterial oxygen saturations;

smooth the arterial oxygen saturations to obtain a smoothed arterial oxygen saturation; and calculate an oxygen saturation in blood based on the smoothed arterial oxygen saturation.

6. The pulse oximeter as set forth in claim 4, wherein:

the processor is operable to:

smooth the gradients to obtain a smoothed gradient;

calculate an arterial oxygen saturation from the smoothed gradient; and calculate an oxygen saturation in blood based on the arterial oxygen saturation.

\* \* \* \* \*